(12) United States Patent
Takei et al.

(10) Patent No.: US 11,846,603 B2
(45) Date of Patent: Dec. 19, 2023

(54) CHEMICAL SENSOR

(71) Applicant: UNIVERSITY PUBLIC CORPORATION OSAKA, Osaka (JP)

(72) Inventors: Kuniharu Takei, Sakai (JP); Shogo Nakata, Sakai (JP)

(73) Assignee: UNIVERSITY PUBLIC CORPORATION OSAKA, Osaka (JP)

( * ) Notice: Subject to any disclaimer, the term of this patent is extended or adjusted under 35 U.S.C. 154(b) by 616 days.

(21) Appl. No.: 17/055,694

(22) PCT Filed: May 22, 2019

(86) PCT No.: PCT/JP2019/020315
§ 371 (c)(1),
(2) Date: Nov. 16, 2020

(87) PCT Pub. No.: WO2019/225660
PCT Pub. Date: Nov. 28, 2019

(65) Prior Publication Data
US 2021/0190722 A1 Jun. 24, 2021

(30) Foreign Application Priority Data

May 25, 2018 (JP) .................. 2018-100611

(51) Int. Cl.
*G01N 27/414* (2006.01)
*G01N 27/333* (2006.01)

(52) U.S. Cl.
CPC ......... *G01N 27/414* (2013.01); *G01N 27/333* (2013.01)

(58) Field of Classification Search
CPC ............... G01N 27/414; G01N 27/333; A61B 5/14517; A61B 5/14546; A61B 5/14539
See application file for complete search history.

(56) References Cited

U.S. PATENT DOCUMENTS

2006/0129332 A1* 6/2006 Mimura ............ G01N 27/4148
702/23
2013/0273664 A1 10/2013 Toumazou et al.

FOREIGN PATENT DOCUMENTS

JP 2002-098667 A 4/2002
JP 2006-189416 A 7/2006
(Continued)

OTHER PUBLICATIONS

Nakata, S., et al., "Flexible Integrated Chemical and Physical Sensors toward a Wearable Healthcare Patch," Transducers 2017, Kaohsiung Taiwan, Jun. 18-22, 2017, p. 1688-1691.

*Primary Examiner* — Mohammed R Alam
(74) *Attorney, Agent, or Firm* — STITES & HARBISON PLLC; Jeffrey A. Haeberlin (57) ABSTRACT

The present invention provides a chemical sensor that can be manufactured at low cost and has high detection sensitivity. The chemical sensor according to the present invention is characterized by comprising: a substrate; a semiconductor thin film having a first contact region and a second contact region; an injection electrode; a first MIS structure; a second MIS structure; a transfer electrode; and a capacitor, wherein the semiconductor thin film has a sensing region provided so that an electric potential thereof changes in direct or indirect response to an object to be measured; the injection electrode is configured to inject an electrical charge into the first contact region; the first MIS structure is configured to control a flow of the electrical charge to the sensing region, the electrical charge being injected into the first contact region by the injection electrode; the second MIS structure is configured to control the flow of the electrical charge from the sensing region to the second contact region; and the (Continued)

transfer electrode is configured to allow the electrical charge in the sensing region to flow to the capacitor through the second contact region.

7 Claims, 6 Drawing Sheets

(56) References Cited

FOREIGN PATENT DOCUMENTS

| | | |
|---|---|---|
| JP | 2008-215974 A | 9/2008 |
| JP | 2013-539049 A | 10/2013 |

* cited by examiner

CHEMICAL SENSOR

TECHNICAL FIELD

The present invention relates to a chemical sensor.

BACKGROUND ART

Ion-sensitive transistors have been known as chemical sensors that are configured to detect ions in a solution (see, for example, PTL 1). Such transistors can be used to detect pH of the solution. However, such pH sensors have a problem of low detection sensitivity.

Also, accumulative chemical/physical phenomenon detection devices have been known (see, for example, PTL 2).

CITATION LIST

Patent Literature

PTL 1: Japanese Unexamined Patent Application Publication No. 2008-215974
PTL 2: Japanese Unexamined Patent Application Publication No. 2002-098667

SUMMARY OF INVENTION

Technical Problem

The traditional chemical sensor has a transistor and others formed on a silicon substrate. The silicon substrate, however, has a problem of a high production cost of the chemical sensor and a problem of difficulty in attaching the chemical sensor to a curved surface or the skin.

The present invention was devised in view of such circumstances, and provides a chemical sensor that can be manufactured at low cost and has high detection sensitivity.

Solution to Problem

The present invention provides a chemical sensor characterized by comprising: a substrate; a semiconductor thin film provided on the substrate and having a first contact region and a second contact region; an injection electrode in contact with the first contact region; a first MIS structure including a part of the semiconductor thin film and a first gate electrode; a second MIS structure including a part of the semiconductor thin film and a second gate electrode; a transfer electrode in contact with the second contact region; and a capacitor electrically connected to the transfer electrode, wherein the semiconductor thin film has a sensing region provided so that an electric potential thereof changes in direct or indirect response to an object to be measured; the injection electrode is configured to inject an electrical charge into the first contact region; the first MIS structure is configured to control a flow of the electrical charge to the sensing region, the electrical charge being injected into the first contact region by the injection electrode; the second MIS structure is configured to control the flow of the electrical charge from the sensing region to the second contact region; and the transfer electrode is configured to allow the electrical charge in the sensing region to flow to the capacitor through the second contact region.

Advantageous Effects of Invention

The chemical sensor of the present invention has the substrate and the semiconductor thin film disposed on the substrate. This makes it possible to use a flexible substrate as the substrate and to attach the flexible substrate to a curved surface or the skin. Also, using the semiconductor thin film, a production cost of the chemical sensor can be reduced.

The semiconductor thin film has the sensing region disposed so that the electric potential thereof changes in direct or indirect response to the object to be measured. The chemical sensor of the present invention also has the first MIS structure and the second MIS structure, the first MIS structure being configured to control the flow of the electrical charge to the sensing region, which was injected into the semiconductor thin film by the injection electrode, and the second MIS structure being configured to control the flow of the electrical charge in the sensing region to the transfer electrode. The first MIS structure configured to control the flow of the electrical charge into the sensing region allows for the injection of the electrical charge from the injection electrode into the sensing region in an amount corresponding to the electric potential of the sensing region that has responded to the object to be measured, and also allows for the storage of the injected electrical charge in the sensing region. The amount of the electrical charge stored in the sensing region is comparable to an amount of an object to be detected. The second MIS structure configured to control the flow of the electrical charge from the sensing region to the transfer electrode allows for the transfer of the electrical charge stored in the sensing region to the capacitor through the transfer electrode. By reading the electrical charge (quantity of electricity) stored in the capacitor as a signal voltage, the object to be detected (for example, pH of the solution) can be detected. Furthermore, by repeating the storage of the electrical charge in the sensing region and the transfer of the electrical charge to the capacitor multiple times, the electrical charges stored in the sensing region can be accumulated in the capacitor, thus increasing the quantity of electrons in the capacitor. This makes it possible to read out the amplified signal voltage, thus increasing detection sensitivity of the chemical sensor.

DESCRIPTION OF EMBODIMENTS

A chemical sensor according to the present invention comprises: a substrate; a semiconductor thin film provided on the substrate and having a first contact region and a second contact region; an injection electrode in contact with the first contact region; a first MIS structure including a part of the semiconductor thin film and a first gate electrode; a second MIS structure including a part of the semiconductor thin film and a second gate electrode; a transfer electrode in contact with the second contact region; and a capacitor electrically connected to the transfer electrode, wherein the semiconductor thin film has a sensing region provided so that an electric potential thereof changes in direct or indirect response to an object to be measured; the injection electrode is configured to inject an electrical charge into the first contact region; the first MIS structure is configured to control a flow of the electrical charge to the sensing region, the electrical charge being injected into the first contact region by the injection electrode; the second MIS structure is configured to control the flow of the electrical charge from the sensing region to the second contact region; and the transfer electrode is configured to allow the electrical charge in the sensing region to flow to the capacitor through the second contact region.

The MIS structure is formed of a three-layer structure including a metal layer, an insulator layer, and a semiconductor layer.

It is desirable that the substrate should be a flexible substrate. This makes it possible to attach the chemical sensor of the present invention to a curved surface or the skin.

It is desirable that the semiconductor thin film should have a thickness that is the same as or thicker than a thickness of a monoatomic layer but is 200 nm or less. This makes it possible to reduce a cost of production of the chemical sensor. Also, this allows the chemical sensor of the present invention to adhere to the curved surface or the skin.

It is desirable that the chemical sensor of the present invention should comprise an extension gate electrode and a third MIS structure. It is desirable that the extension gate electrode should comprise a gate portion and a sensing section that electrically interacts directly or indirectly with the object to be measured. It is desirable that the third MIS structure should include the sensing region of the semiconductor thin film and the gate portion. Such a structure as above is capable of arranging the sensing section, which interacts electrically with the object to be measured, separately from a charge transfer section comprising the MIS structures, thereby preventing the object to be measured adversely affecting the charge transfer section.

It is desirable that the chemical sensor of the present invention should be provided with a reference electrode. It is desirable that the reference electrode should be placed around the sensing section of the extension gate electrode. This placement of the reference electrode enables the reference electrode to come in contact with an aqueous solution as the object to be measured, thereby giving a reference point to the electric potential of the aqueous solution.

It is desirable that the chemical sensor of the present invention should comprise a fourth MIS structure. It is desirable that the fourth MIS structure should include the first contact region of the semiconductor thin film and a third gate electrode. Applying a gate voltage to this third gate electrode can change an electric potential in the first contact region, leading to a decrease in a Schottky barrier formed between the injection electrode and the first contact region.

It is desirable that the chemical sensor of the present invention should comprise a fifth MIS structure. It is desirable that the fifth MIS structure should include the second contact region of the semiconductor thin film and a fourth gate electrode. It is desirable that the transfer electrode should be in contact with the second contact region of the semiconductor thin film. Applying a gate voltage to this fourth gate electrode can change an electric potential in the second contact region, thereby enabling a Schottky barrier formed between the transfer electrode and the second contact region to decrease.

Hereinafter, an Embodiment of the present invention will be described with reference to the accompanying drawings. Structures shown in the drawings or described below should be recognized as exemplifications in all respects, and the scope of the present invention is not limited to the drawings and the following descriptions.

Figure 1:
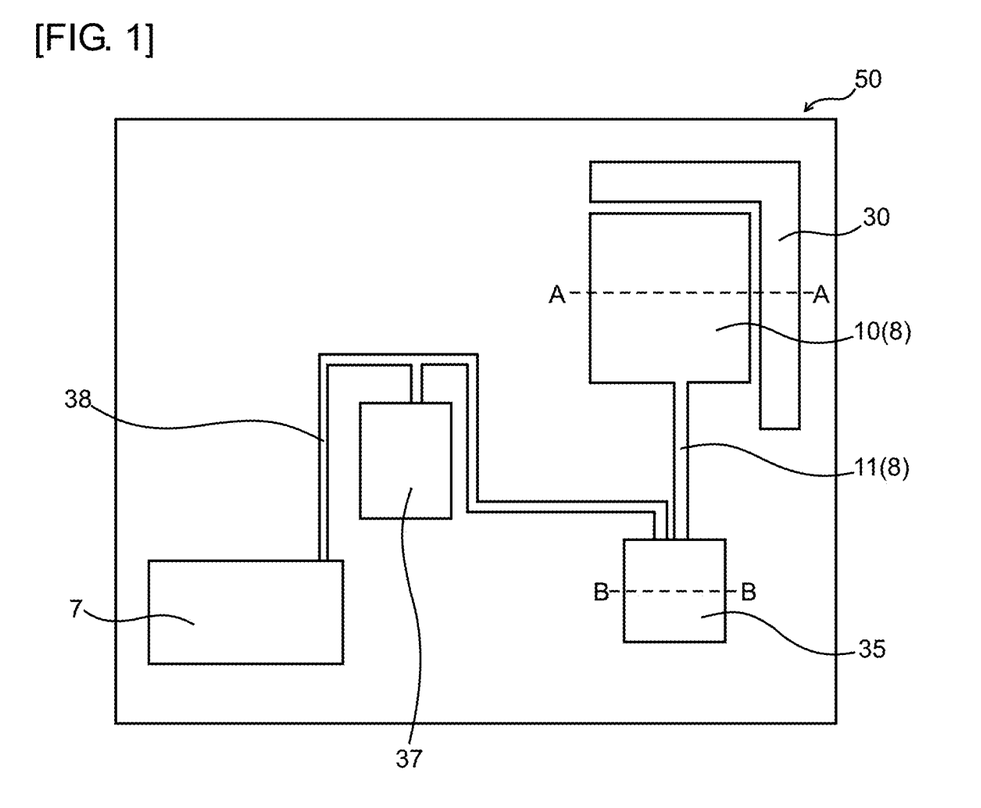
FIG. 1 is a diagrammatic top view of a chemical sensor in accordance with an Embodiment of the present invention.
Figure 3:
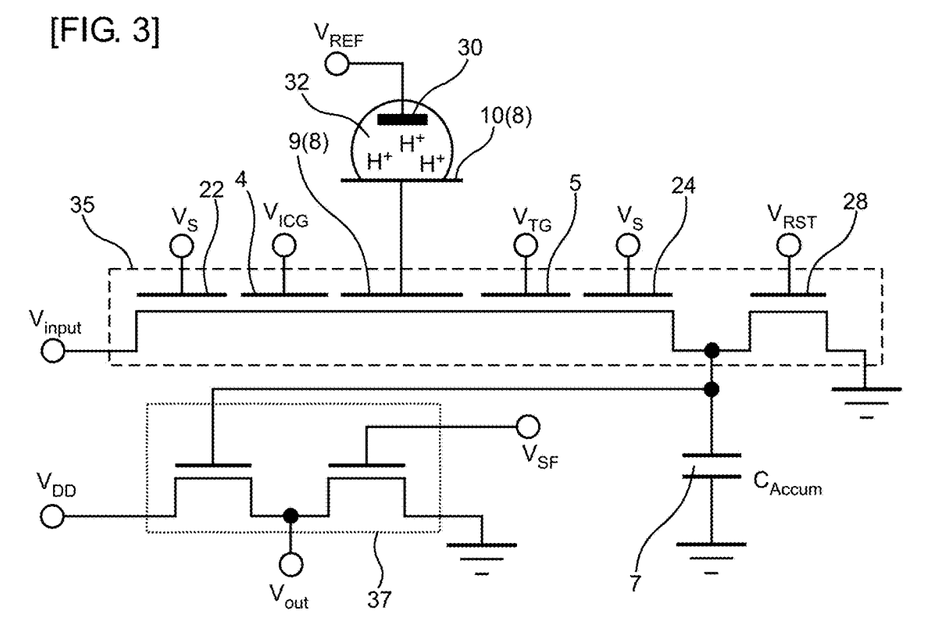
FIG. 3 is a diagrammatic view of an electric circuit of a chemical sensor in accordance with an Embodiment of the present invention.
Figure 4:
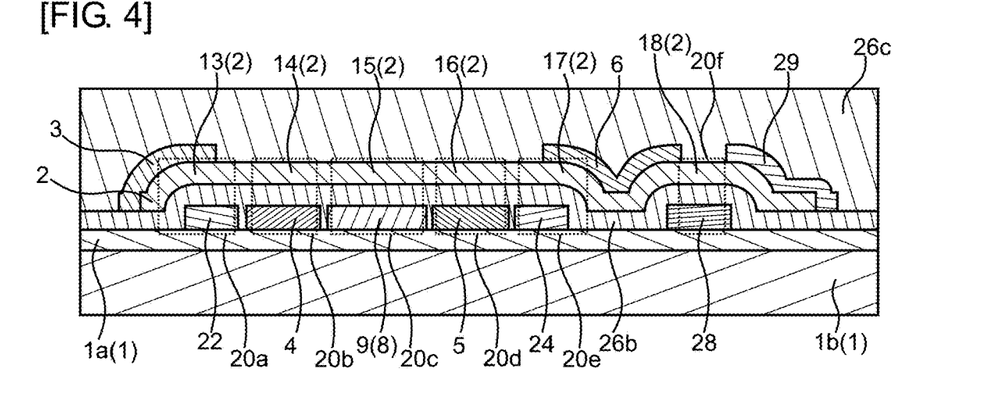
FIG. 4 is a diagrammatic cross-section view of a chemical sensor in accordance with an Embodiment of the present invention.
Figure 5:
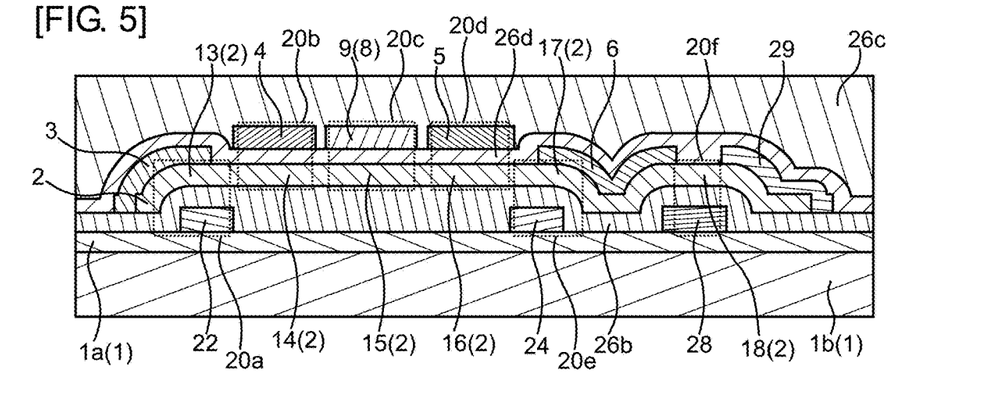
FIG. 5 is a diagrammatic cross-section view of a chemical sensor in accordance with an Embodiment of the present invention.
Figure 6:
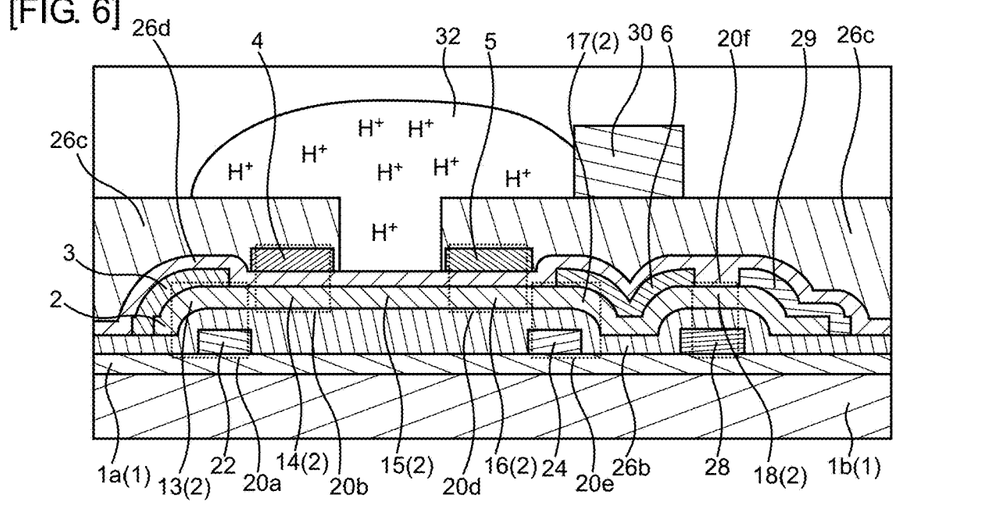
FIG. 6 is a diagrammatic cross-section view of a chemical sensor in accordance with an Embodiment of the present invention.

FIG. 1 is a diagrammatic top view of a chemical sensor in accordance with the present Embodiment. FIG. 2(a) is a diagrammatic cross-section view of the chemical sensor taken along the dashed line A-A of FIG. 1; and FIG. 2(b) is a diagrammatic cross-section view of the chemical sensor taken along the dashed line B-B of FIG. 1. FIG. 3 is a diagrammatic view of an electric circuit of a chemical sensor in accordance with the present Embodiment. FIG. 4 to FIG. 6 show diagrammatic cross-section views of chemical sensors in accordance with the present Embodiments, respectively.

A chemical sensor 50 in accordance with the present Embodiment is characterized by comprising: a substrate 1; a semiconductor thin film 2 provided on the substrate 1 and having a first contact region 13 and a second contact region 17; an injection electrode 3 in contact with the first contact region 13; an MIS structure 20b including a part of the semiconductor thin film 2 and a first gate electrode 4; an MIS structure 20d including a part of the semiconductor thin film 2 and a second gate electrode 5; a transfer electrode 6 in contact with the second contact region 17; and a capacitor 7 electrically connected to the transfer electrode 6, wherein the semiconductor thin film 2 has a sensing region 15 provided so that an electric potential thereof changes in direct or indirect response to an object 32 to be measured; the injection electrode 3 is configured to inject an electrical charge into the first contact region 13; the MIS structure 20b is configured to control a flow of the electrical charge to the sensing region 15, the electrical charge being injected into the first contact region 13 by the injection electrode 3; the MIS structure 20d is configured to control the flow of the electrical charge from the sensing region 15 to the second contact region 17; and the transfer electrode 6 is configured to allow the electrical charge in the sensing region 15 to flow to the capacitor 7 through the second contact region 17.

The chemical sensor 50 in accordance with the present Embodiment can comprise at least one of a source follower circuit 37, a reference electrode 30, a reset gate electrode 28, and a reset electrode 29.

A charge transfer section 35 includes the semiconductor thin film 2, the injection electrode 3, the first gate electrode 4, the second gate electrode 5, the transfer electrode 6, a gate portion 9 of an extension gate electrode 8, a third gate electrode 22, a fourth gate electrode 24, the reset gate electrode 28, and the reset electrode 29.

Hereinafter, the chemical sensor 50 in accordance with the present Embodiment will be described.

The chemical sensor 50 is a sensor configured to detect chemical substances. Specific examples of the sensor include an ion sensor (including a pH sensor), which is configured to detect ions in a solution, and a wearable sensor, which is configured to detect chemical substances contained in sweat secreted from sweat glands (including pH of the sweat) or chemical substances released from the skin. The chemical sensor 50 may be a flexible sensor.

The substrate 1 is made of a plate or a sheet that functions as a basic component of the chemical sensor 50. The substrate 1 may be a flexible substrate. This makes the chemical sensor 50 be the flexible sensor, and makes it possible to stick the chemical sensor 50 on a curved surface, the skin, and so forth.

The substrate 1 may be formed of a laminate structure. For example, the substrate 1 of the chemical sensor 50 shown in FIGS. 2 and 4 to 6 comprises a substrate 1a and a substrate 1b. The substrate 1a is made of, for example, a polyimide sheet; and the substrate 1b is made of a PET (polyethylene terephthalate) sheet. Due to its heat resistance, the polyimide sheet can be used as the basic component of the chemical sensor 50 at a time of preparing the chemical sensor 50. The PET sheet functions as a support sheet of the polyimide sheet.

The semiconductor thin film 2 is a thin film of a semiconductor to be disposed on the substrate 1. There may be an insulator layer 26 and the gate electrodes placed between the substrate 1 and the semiconductor thin film 2. The semiconductor thin film 2 has a thickness that is, for example, the same as or thicker than a thickness of a monoatomic layer but is 200 nm or less. The semiconductor thin film 2 may be an n-type semiconductor or may be a p-type semiconductor. The semiconductor thin film 2 is made of, for example, an oxide semiconductor thin film, a silicon thin film, a carbon nanotube thin film, or an organic semiconductor thin film. As examples of a material for the oxide semiconductor thin film, there may be mentioned IGZO(In—Ga—Zn—O), ITZO(In—Sn—Zn—O), and IGO (In—Ga—O).

The semiconductor thin film 2 may have the first contact region 13, a first control region 14, the sensing region 15, a second control region 16, and the second contact region 17.

The injection electrode 3 is disposed in such a way as to be in contact with the first contact region 13 of the semiconductor thin film 2. The injection electrode 3 is disposed in such a way as to inject an electrical charge (electrons) into the first contact region 13 of the semiconductor thin film 2. The injection electrode 3 may be disposed under the semiconductor thin film 2 or on the semiconductor thin film 2. To the injection electrode 3, a voltage $V_{input}$ is applied in such a way as to inject the electrical charge into the first contact region 13.

The injection electrode 3 may be made of a metal monolayer film or a metal laminated film. The injection electrode 3 may have, for example, an Au layer (which is in contact with the semiconductor thin film).

The third gate electrode 22 may be disposed in such a way that the first contact region 13 of the semiconductor thin film 2 is placed between the injection electrode 3 and the third gate electrode 22. The third gate electrode 22 together with the first contact region 13 of the semiconductor thin film 2 and a gate insulating film may be disposed so as to configure an MIS structure 20a (which is a three-layer structure including a metal layer, an insulator layer, and a semiconductor layer). When a gate voltage is applied to the third gate electrode 22 having the structure described above, an electric potential in the first contact region 13 is changed. For example, even when a Schottky barrier is formed at an interface between the injection electrode 3 and the first contact region 13, a height of the Schottky barrier can be lowered by applying the gate voltage to the third gate electrode 22, with the result that the electrical charge is more easily injected into the first contact region 13 from the injection electrode 3. The third gate electrode 22 may be omitted.

Figure 2:
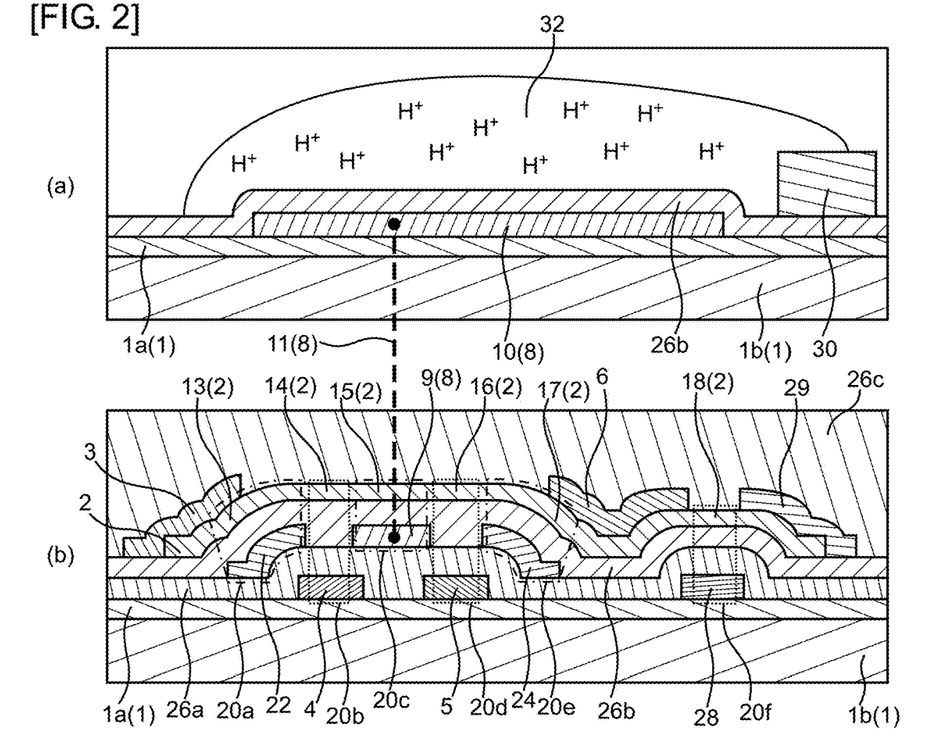
FIG. 2(a) is a diagrammatic cross-section view of the chemical sensor taken along the dashed line A-A of FIG. 1.
FIG. 2(b) is a diagrammatic cross-section view of the chemical sensor taken along the dashed line B-B of FIG. 1.

In FIG. 2(*b*) and FIG. 4 to FIG. 6, for example, an insulator layer 26b becomes a gate insulating film of the MIS structure 20a. In FIG. 2 and FIG. 4 to FIG. 6, the third gate electrode 22 is positioned on the lower side of the semiconductor thin film 2, and the injection electrode 3 is positioned on the upper side of the semiconductor thin film 2; however, the third gate electrode 22 may be positioned on the upper side of the semiconductor thin film 2, and the injection electrode 3 may be positioned on the lower side of the semiconductor thin film 2.

The gate electrode (the first gate electrode 4, the second gate electrode 5, the third gate electrode 22, the fourth gate electrode 24, the reset gate electrode 28, or the gate portion 9 of the extension gate electrode 8) may be made of a metal monolayer film or a metal laminated film made from a plurality of metals. The gate electrode may be, for example, an Al electrode.

The insulator layer 26 (insulator layer 26a, 26b, 26c, or 26d) is a layer made of an insulator. A material for the insulator layer 26 may be an inorganic insulator or an organic insulator. As examples of the material for the insulator layer 26a, 26b, or 26d to function as a gate insulating film, there may be mentioned $SiO_2$, $Al_2O_3$, and $Si_3N_4$. The insulator layer 26a, 26b, or 26d may be made of a monolayer film or a laminated film comprising a plurality of insulators. The material for the insulator layer 26c that covers upper parts of the MIS structures may be an organic insulator such as a polyimide.

As shown in FIG. 2(*b*), the insulator layers 26 to function as the gate insulating films of the plurality of MIS structures (each of which having a three-layer structure including a metal layer, an insulator layer, and a semiconductor layer) may have a two-layer structure including the insulator layer 26b, which comes in contact with the semiconductor thin film 2, and the insulator layer 26a, which comes in contact with the insulator layer 26b. Some of the plurality of gate electrodes may be placed between the insulator layer 26a and the insulator layer 26b, and the other gate electrodes may be placed on a side of insulator layer 26a opposite to the insulator layer 26b. One of the two adjacent gate electrodes may be placed between the insulator layer 26a and the insulator layer 26b, and the other one may be placed on a side of insulator layer 26a opposite to the insulator layer 26b. This makes it possible to place the insulator layer 26a between the two adjacent gate electrodes, thereby inhibiting leak current from flowing between the gate electrodes. The two adjacent gate electrodes may be arranged in such a way that one end of the gate electrode may overlap with one end of the other gate electrode. This makes it possible to prevent any interspace (gap) between the regions (the first contact region 13, the first control region 14, the sensing region 15, the second control region 16, or the second contact region 17) of the semiconductor thin film 2.

In FIG. 2(*b*), the two-layer structure including the gate insulating films and every gate electrode are arranged below the semiconductor thin film 2; however, the two-layer structure including the gate insulating films and every gate electrode may be arranged above the semiconductor thin film 2.

The first gate electrode 4 is arranged in such a way that the first gate electrode 4, the first control region 14 of the semiconductor thin film 2, and the gate insulating film(s) configure the MIS structure 20b. For example, FIG. 2(b) shows that the insulator layer 26a and the insulator layer 26b become the gate insulating films; FIG. 4 shows that the insulator layer 26b becomes the gate insulating film; and FIG. 5 and FIG. 6 show that the insulator layer 26d becomes the gate insulating film. By applying a gate voltage to the first gate electrode 4, an electric potential in the first control region 14 of the semiconductor thin film 2 included in the MIS structure 20b can be changed.

The MIS structure 20b is configured to control a flow of an electrical charge to the sensing region 15, the electrical charge being injected into the first contact region 13 by the injection electrode 3. By controlling a gate voltage $V_{ICG}$ to be applied to the first gate electrode 4, it is possible to limit or promote a flow of the electrical charge from the first contact region 13 to the sensing region 15.

The MIS structure 20b is configured so that the first control region 14 is placed between the first contact region 13 and the sensing region 15. This makes it possible to control the flow of the electrical charge into the sensing region 15.

The first gate electrode 4 may be located below the semiconductor thin film 2, as shown in FIG. 2(b) and FIG. 4, or may be located above the semiconductor thin film 2, as shown in FIGS. 5 and 6.

The sensing region 15 of the semiconductor thin film 2 is provided so that an electric potential thereof changes in direct or indirect response to the object 32 to be measured. In FIG. 2 to FIG. 5, the sensing region 15 is configured to respond indirectly to the object 32 to be measured with use of the extension gate electrode 8. In FIG. 6, the sensing region 15 of the semiconductor thin film 2 is configured to respond directly to the object 32 to be measured.

The extension gate electrode 8 has the gate portion 9, a sensing section 10, and a wiring portion 11 connecting the gate portion 9 to the sensing section 10. The extension gate electrode 8 may be, for example, an Al electrode.

The gate portion 9 is arranged in such a way that the gate portion 9, the sensing region 15 of the semiconductor thin film 2, and the gate insulating film configure an MIS structure 20c. In FIG. 2(b) and FIG. 4, for example, the insulator layer 26b becomes the gate insulating film. In FIG. 5, the insulator layer 26d becomes a gate insulating film. The MIS structure 20c is configured so that the sensing region 15 of the semiconductor thin film 2 is placed between the first control region 14 and the second control region 16. The gate portion 9 may be disposed below the semiconductor thin film 2, as shown in FIG. 2(b) and FIG. 4, or may be disposed above the semiconductor thin film 2, as shown in FIG. 5.

The sensing section 10 is configured to electrically interact directly or indirectly with the object 32 to be measured. Examples of the object 32 to be measured include an aqueous solution, sweat, and chemical substances released from the skin (for example, acetone).

For example, in the case where the object 32 to be measured is the aqueous solution, and an object to be detected is pH of this aqueous solution, the sensing section 10 is provided so as to electrically interact with hydrogen ions ($H^+$) in the aqueous solution. The sensing section 10, as shown in FIG. 2(a), for example, may be configured to electrically interact with the aqueous solution through the insulator layer 26b. Also, the sensing section 10 may have the reference electrode 30 placed therearound. The reference electrode 30 is placed so as to come in contact with the object 32 to be measured. In a case where an electric potential of the reference electrode 30 is constant, and a concentration of hydrogen ions in the aqueous solution changes, a difference in electric potentials between the aqueous solution and the sensing section 10 changes in a three-layer structure including the aqueous solution, the insulator layer 26b, and the sensing section 10. Thus an electric potential in the sensing section 10 changes according to the concentration of the hydrogen ions in the aqueous solution.

The reference electrode 30 may be, for example, an Ag/AgCl reference electrode.

Since the sensing section 10 is connected to the gate portion 9 through the wiring portion 11, the sensing section 10 and the gate portion 9 are substantially the same in electric potential. Since the sensing region 15 of the semiconductor thin film 2, the gate insulating film, and the gate portion 9 configure the MIS structure 20c, an electric potential in the sensing region 15 can be changed by the electric potential in the gate portion 9. Therefore, the electric potential of the sensing region 15 of the semiconductor thin film 2 changes in indirect response to the object 32 to be measured.

The chemical sensor shown in FIG. 6 is configured in such a way that the sensing region 2 of the semiconductor thin film 2 interacts electrically with the hydrogen ions ($H^+$) in the aqueous solution (the object 32 to be measured) through the insulator film 26d without using the extension gate electrode 8. The reference electrode 30 is disposed so as to come in contact with the object 32 to be measured. In a case where an electric potential in the reference electrode 30 is constant, and a concentration of the hydrogen ions in the aqueous solution changes, a difference in electric potentials between the aqueous solution and the sensing region 15 changes in a three-layer structure including the aqueous solution, the insulator layer 26d, and the sensing region 15. Thus an electric potential in the sensing region 15 changes in response to the concentration of the hydrogen ions in the aqueous solution. The electric potential in the sensing region 15 of the semiconductor thin film 2 is then changed in direct response to the object 32 to be measured.

The change in this way in the electric potential in the sensing region 15 of the semiconductor thin film 2 in direct or indirect response to the object 32 to be measured enables an amount of the electrical charge corresponding to this electric potential responded to flow from the injection electrode 3 to the sensing region 15 through the first contact region 13 and the first control region 14. Since this amount of the electrical charge that flowed into the sensing region corresponds to the object 32 to be measured, this electrical charge is transferred to the capacitor 7, with the result that a quantity of electricity in the capacitor 7 can be detected, and then pH and others of the object 32 can be detected. Furthermore, the amount of the electrical charge in the sensing region may be transferred to the capacitor 7 more than once, and the electrical charges may be accumulated in the capacitor 7, thereby increasing a quantity of the electricity in the capacitor 7, and thus increasing detection sensitivity of the chemical sensor 50.

The chemical sensor 50 configured to detect the chemical substances may have a sensitive film on the sensing section 10 of the extension gate electrode 8, the sensitive film being responsive to the chemical substances. The sensitive film may have, for example, a catalyst and an adsorbent. The sensitive film is configured to supply an electrical charge to the sensing section 10 once the catalyst, the adsorbent, and so forth react to the chemical substances, which are the objects to be detected. This allows an electric potential in the extension gate electrode 8 and an electric potential in the sensing region 15 of the semiconductor thin film 2 to change according to amounts of the chemical substances, i.e., the objects to be detected, thereby enabling the chemical sensor 50 to detect the chemical substances.

The second gate electrode 5 is arranged in such a way that the second gate electrode 5, the second control region 16 of the semiconductor thin film 2, and the gate insulating film(s) configure the MIS structure 20d. For example, FIG. 2(b) shows that the insulator layer 26a and the insulator layer 26b become the gate insulating films; FIG. 4 shows that the insulator layer 26b becomes the gate insulating film; and FIG. 5 and FIG. 6 show that the insulator layer 26d becomes the gate insulating film. By applying a gate voltage to the second gate electrode 5, an electric potential in the second control region 16 of the semiconductor thin film 2 included in the MIS structure 20d can change.

The MIS structure 20d is configured to control a flow, to the transfer electrode 6, of an electrical charge in the sensing region 15 of the semiconductor thin film 2. By controlling a gate voltage $V_{TG}$ to be applied to the second gate electrode 5, it is possible to limit or promote a flow of the electrical charge from the sensing region 15 to the transfer electrode 6. The MIS structure 20d is provided so that the second control region 16 is placed between the sensing region 15 and the second contact region 17. This allows the flow of the electrical charge from the sensing region 15 to the second contact region 17 to be controlled.

The second gate electrode 5 may be positioned below the semiconductor thin film 2, as shown in FIG. 2(b) and FIG. 4, or may be positioned above the semiconductor thin film 2, as shown in FIGS. 5 and 6.

The gate portion 9 of the extension gate electrode 8, the first gate electrode 4, and the second gate electrode 5 may all be positioned either above or below the semiconductor thin film 2. This allows an electric potential in the semiconductor thin film 2 at an interface between the semiconductor thin film 2 and the gate insulating film to be changed by the gate portion 9, the first gate electrode 4, and the second gate electrode 5.

The transfer electrode 6 is placed so as to be in contact with the second contact region 17 of the semiconductor thin film 2. The transfer electrode 6 is electrically connected to the capacitor 7. The transfer electrode 6 is provided so as to allow the electrical charge in the sensing region 15 to flow to the capacitor 7 through the second control region 16 and the second contact region 17. The transfer electrode 6 may also be electrically connected to the source follower circuit 37. The transfer electrode 6 may be placed beneath the semiconductor thin film 2 or on the semiconductor thin film 2.

The transfer electrode 6 may be made of a metal monolayer film or a metal laminated film. The transfer electrode 6 may have, for example, an Au layer (which is in contact with the semiconductor thin film 2).

The fourth gate electrode 24 may be provided so that the second contact region 17 of the semiconductor thin film 2 is placed between the transfer electrode 6 and the fourth gate electrode 24. The fourth gate electrode 24 together with the second contact region 17 of the semiconductor thin film 2 and the gate insulating film can be provided so as to configure an MIS structure 20e (which is a three-layer structure including a metal layer, an insulator layer, and a semiconductor layer). Upon applying a gate voltage to the fourth gate electrode 24 having the structure as above, an electric potential in the second contact region 17 is changed. For example, even when a Schottky barrier is formed at an interface between the transfer electrode 6 and the second contact region 17, it is possible to lower the Schottky barrier by applying the gate voltage to the fourth gate electrode 24, with the result that the electrical charge in the second contact region 17 can easily flow into the transfer electrode 6. The fourth gate electrode 24 may be omitted.

In FIG. 2(b) and FIG. 4 to FIG. 6, for example, the insulator layer 26b becomes the gate insulating film of the MIS structure 20e. In FIG. 2 and FIG. 4 to FIG. 6, the fourth gate electrode 24 is positioned below the semiconductor thin film 2, and the transfer electrode 6 is positioned above the semiconductor thin film 2; however, the fourth gate electrode 24 may be positioned above the semiconductor thin film 2, and the transfer electrode 6 may be positioned below the semiconductor thin film 2.

The capacitor 7 comprises a first conductive layer, a second conductive layer, and an insulator layer (dielectric layer), which is disposed between the first conductive layer and the second conductive layer. One of the first conductive layer and the second conductive layer may be electrically connected to the transfer electrode 6; and the other conductive layer may be electrically connected to a ground. This allows an electrical charge in the sensing region 15 to be transferred to the capacitor 7 through the transfer electrode 6. This also allows the electrical charge in the sensing region 15 to be transferred to the capacitor 7 more than once, and thus enables the electrical charges to be accumulated in the capacitor 7. The capacitor 7, for example, may be electrically connected to the transfer electrode 6 through a wiring 38, as shown in FIG. 1.

The source follower circuit 37 is a circuit for reading a quantity of electricity of the capacitor 7. The source follower circuit 37 is configured to output the quantity of the electricity of capacitor 7 as a signal voltage (output voltage $V_{out}$). The source follower circuit 37 may be electrically connected to, for example, the capacitor 7 and the transfer electrode 6 through the wiring 38, as shown in FIGS. 1 and 3. Also, the source follower circuit 37 may have, for example, an electric circuit as shown in FIG. 3.

The reset electrode 29 may be disposed so as to be in contact with the semiconductor thin film 2. The reset electrode 29 may also be electrically connected to the ground.

The reset gate electrode 28 is arranged in such a way that the reset gate electrode 28, the third control region 18 of the semiconductor thin film 2, and the gate insulating film(s) configure an MIS structure 20f. In FIG. 2(b), for example, the insulator layer 26a and the insulator layer 26b become the gate insulating films; and in FIGS. 4 to 6, the insulator layer 26b becomes the gate insulating film. Applying a gate voltage to the reset gate electrode 28 can change an electric potential in the third control region 18 of the semiconductor thin film 2 included in the MIS structure 20f.

The MIS structure 20f may be configured to control a flow of an electrical charge from the second contact region 17 and the transfer electrode 6 to the reset electrode 29. This makes it possible to control a gate voltage $V_{RST}$ to be applied to the reset gate electrode 28, with the result that it is possible to limit the flow of the electrical charge from the second contact region 17 and the transfer electrode 6 to the reset electrode 29, and to let the electrical charge of the capacitor 7 and the sensing region 15 flow to the ground through the reset electrode 29, thereby resetting the electric potential in the capacitor 7 and the sensing region 15. The MIS structure 20f is configured so that the third control region 18 is placed between the transfer electrode 6 and the reset electrode 29.

Next, a charge transfer mechanism of the chemical sensor 50 in accordance with the present Embodiment will be described using FIG. 7. $V_{input}$ is an electric potential in the injection electrode 3; a region indicated as $V_{ICG}$ is a band diagram of the first control region 14 controlled by the first gate electrode 4; a region indicated as pH is a band diagram of the sensing region 15; and a region indicated as $V_{TG}$ is a band diagram of the second control region 16 controlled by the second gate electrode 5.

FIG. 7(a) shows a band diagram of an initial state. In the state shown in FIG. 7(a), an aqueous solution as the object 32 to be measured has not yet been dropped into the chemical sensor 50.

When the aqueous solution as the object 32 to be measured is dropped into the chemical sensor 50 (see, for example, FIG. 2(a) and FIG. 6), the band diagram changes, as shown in FIG. 7(b). More specifically, an electric potential of the sensing region 15 changes in response to hydrogen ions in the aqueous solution, which is the object 32 to be measured.

Next, the voltage $V_{ICG}$ of the first gate electrode 4 is changed, as shown in FIG. 7(c); and the electrical charge flows from the injection electrode 3 into the sensing region 15. At this time, an amount of the electrical charge comparable to an amount of the hydrogen ions in the aqueous solution, which is the object 32 to be measured, flows into the sensing region 15.

Next, as shown in FIG. 7(d), the voltage $V_{ICG}$ of the first gate electrode 4 is changed so that no electrical charge flows into the sensing region 15. By doing so, the amount of the electrical charge comparable to the amount of the hydrogen ions is confined in the sensing region 15.

Next, as shown in FIGS. 7(e) and 7(f), the voltage $V_{TG}$ of the second gate electrode 5 is changed; and the electrical charge in the sensing region 15 is transferred to the capacitor 7 through the transfer electrode 6.

Then, as shown in FIG. 7(b), the voltage $V_{TG}$ in the second gate electrode 5 is changed so that the electrical charge in the sensing region 15 does not flow into the transfer electrode 6.

By repeating operations (charge transfer cycle) shown in FIG. 7(b), FIG. 7(c), FIG. 7(d), FIG. 7(e), and FIG. 7(f) multiple times in this order, the amount of the electrical charge corresponding to the hydrogen ions in the aqueous solution, which is the object 32 to be measured, can be transferred to the capacitor 7 multiple times, thereby accumulating the electrical charges in the capacitor 7.

The source follower circuit 37 is then used to read out a quantity of electricity in the capacitor 7 as an output voltage $V_{out}$ (signal voltage). Since this output voltage $V_{out}$ is a value that corresponds to the amount of the hydrogen ions in the aqueous solution, which is the object 32 to be measured, pH of the solution can be calculated from the output voltage $V_{out}$ using a calibration curve. Since the charge transfer cycle is repeated multiple times, the amplified signal voltages can be output; and the pH of the aqueous solution, which is the object 32 to be measured, can be detected with high sensitivity. The calibration curve used here is prepared beforehand.

Thereafter, the voltage of the reset gate electrode 28 is changed, and the electrical charges stored in the capacitor 7 and the electrical charge in the sensing region 15 are allowed to flow into the reset electrode 29, restoring the electric potential in the capacitor 7 and the electric potential in the sensing region 15 to their initial state.

The charge transfer cycle is repeated multiple times to read the quantity of the electricity stored in the capacitor 7 and to repeat the measurement cycle multiple times by applying the voltage to the reset gate electrode 28, thereby monitoring changes in the pH of the object 32.

Although the detection of the pH of the solution has been described here, the chemical sensor 50 of the present Embodiment can also be used to detect concentrations of chemical substances contained in sweat secreted by sweat glands and concentrations of chemical substances (such as acetone) released from the skin.

Experiment in Preparation of Chemical Sensor

A chemical sensor (pH sensor) as shown in FIGS. 1 to 3 was prepared as follows.

(1) A polyamide acid solution was spin-coated on an Si/SiO$_2$ handle wafer and was calcinated at 350° C., forming a polyimide layer (10 μm thick or less) (substrate 1a) on the wafer.

(2) By vapor-depositing an Al layer on the polyimide layer and patterning the Al layer using wet etching, a first gate electrode 4, a second gate electrode 5, and a reset gate electrode 28 were formed.

(3) An Al$_2$O$_3$ layer (50 nm thick) and an SiO$_x$ layer (10 nm thick) (insulator layer 26a) were formed on these gate electrodes.

(4) By vapor-depositing an Al layer on the insulator layer 26a and patterning the Al layer using wet etching, a third gate electrode 22, an extension gate electrode 8, and a fourth gate electrode 24 were formed.

(5) An Al$_2$O$_3$ layer (50 nm thick) and an SiO$_x$ layer (10 nm thick) (insulator layer 26b) were formed on these gate electrodes.

(6) An amorphous InGaZnO thin film (30 nm thick) was deposited on the insulator layer 26b using a sputtering method; and a semiconductor thin film 2 was formed by patterning.

(7) By depositing a Cr/Au layer on the semiconductor thing film 2 and patterning the layer, an injection electrode 3, a transfer electrode 6, and a reset electrode 29 were formed.

(8) The laminate thereby formed was heat-treated at 200° C. for 90 minutes in a vacuum atmosphere and then was heat-treated at 250° C. for 20 minutes in a forming gas.

(9) An Ag/AgCl reference electrode ink was applied around a sensing section 10 of the extension gate electrode 8, and was heat-treated at 120° C. for 2 minutes in air, forming a reference electrode 30.

(10) By applying polyimide tapes over areas other than the sensing section 10 of the extension gate electrode 8 and the reference electrode 30, an insulator layer 26c was formed.

(11) The polyimide layer was removed from the Si/SiO$_2$ handle wafer; and a PET film (substrate 1b) with a temperature sensor was attached to the polyimide layer.

A chemical sensor was prepared according to procedures (1) to (11). In procedures (2) to (8), a source follower circuit 37, a capacitor 7, a wiring 38, and so forth are also formed at the same time.

Figure 8:
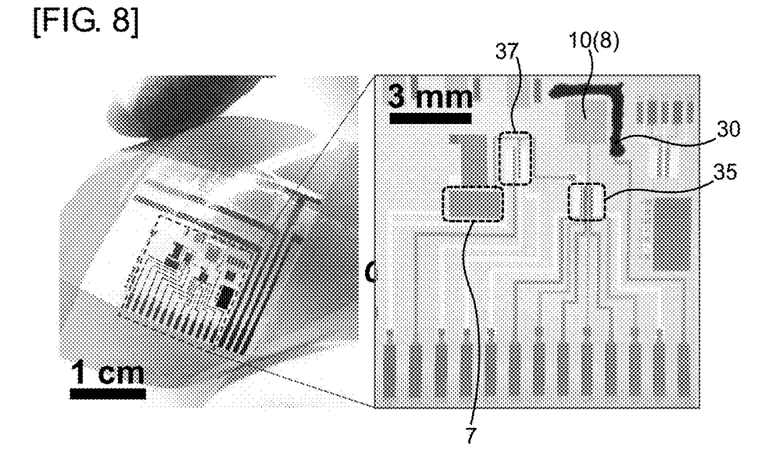
FIG. 8 shows a photograph and an explanatory drawing of a pH sensor prepared.

A photograph of the prepared pH sensor and its explanatory drawing are shown in FIG. 8.

pH Detection Experiment

By using the pH sensor prepared, a relationship between an output voltage $V_{out}$ and a pH of a solution, which is an object to be measured, was analyzed. More specifically, voltage sequences, as shown in FIG. 9(a) to FIG. 9(c), were performed as the aqueous solution with pH pre-adjusted was dropped on the sensing section 10 of the extension gate electrode 8, thereby outputting the output voltage $V_{out}$. The number of charge transfer cycles is changed according to the measurement.

Figure 9:
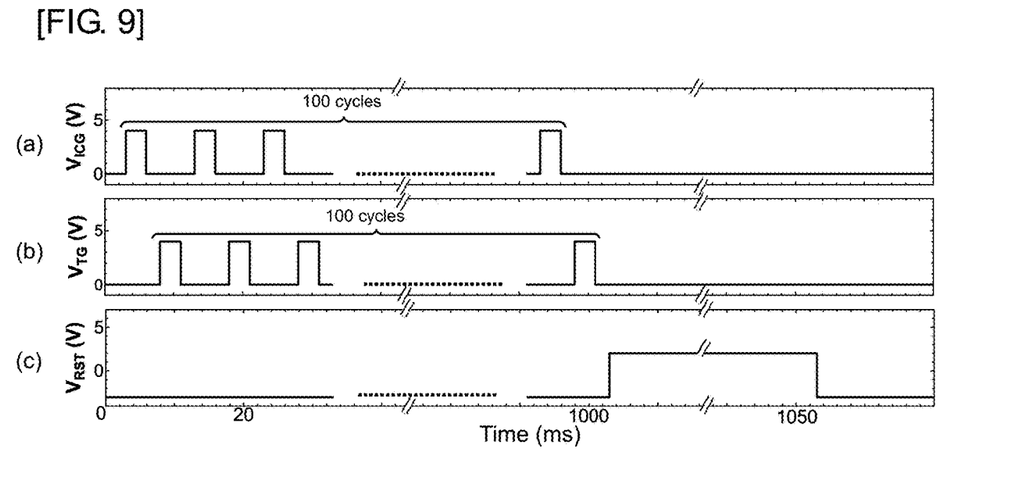
FIGS. 9(a) to 9(c) each show a voltage sequence of one measurement cycle.

FIG. 9(*a*) shows the voltage sequence of a voltage $V_{ICG}$ to be applied to the first gate electrode 4 associated with one measurement cycle; FIG. 9(*b*) shows the voltage sequence of a voltage $V_{TG}$ to be applied to the second gate electrode 5 associated with one measurement cycle; and FIG. 9(*c*) shows the voltage sequence of a voltage $V_{RST}$ to be applied to the reset gate electrode 28 associated with one measurement cycle.

Figure 7:
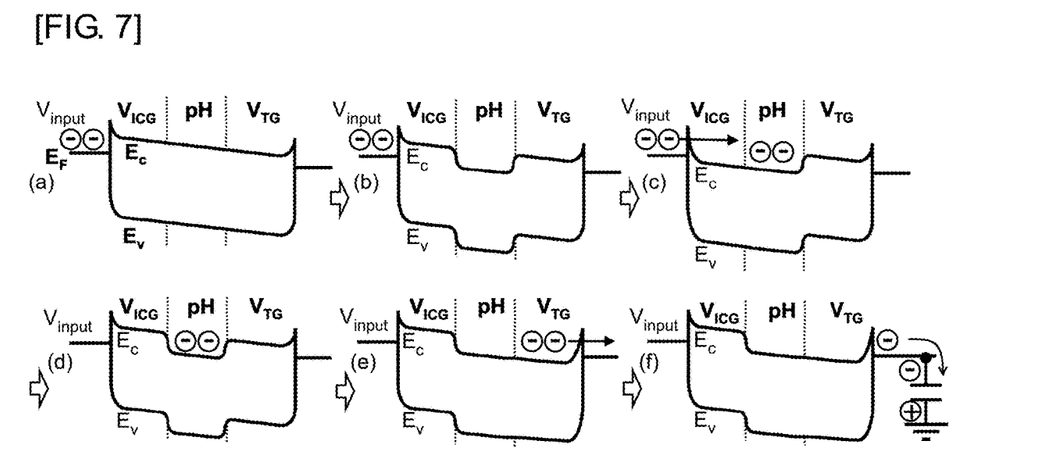
FIG. 7 is an explanatory drawing of a charge transfer in a chemical sensor in accordance with an Embodiment of the present invention.

When a voltage of 4 V is applied to the first gate electrode 4, as shown in FIG. 9(*a*), an electrical charge flows into the sensing region 15, as shown in FIG. 7(*c*). When a voltage of 4 V is applied to the second gate electrode 5, as shown in FIG. 9(*b*), the electrical charge in the sensing region 15 is transferred to the capacitor 7, as shown in FIGS. 7(*e*) and 7(*f*). By repeating such a charge transfer cycle including the application of the voltage to the first gate electrode and to the second gate electrode a plurality of times, the electrical charges are accumulated in the capacitor 7, leading to an increase in quantity of the electricity in the capacitor 7.

After the repetition of the charge transfer cycle is completed, the source follower circuit 37 outputs the quantity of the electricity in the capacitor 7 as the output voltage (signal voltage) $V_{out}$.

After the output voltage $V_{out}$ is outputted, a voltage of 2 V is applied to the reset gate electrode 28, as shown in FIG. 9(*c*); and the electrical charge of the capacitor 7 and the sensing region 15 flows to ground.

Figure 10:
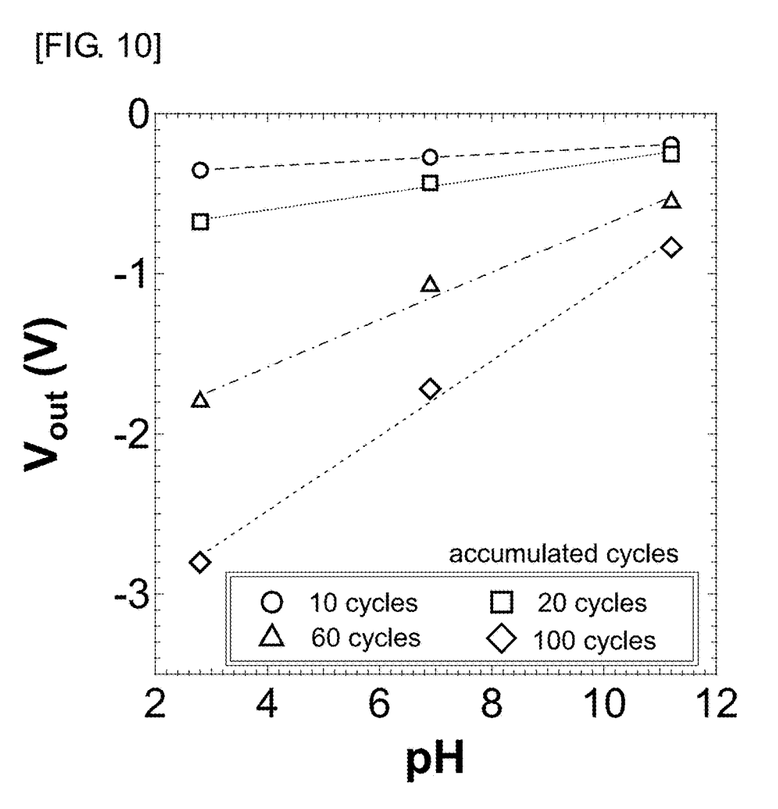
FIG. 10 shows a graph of results of pH detection experiments.

FIG. 10 is a graph showing the experimental results and the relationship between the output voltage $V_{out}$ and the pH of the aqueous solution, which is the object measured. As the object measured, a pH 2.8 aqueous solution, a pH 6.9 aqueous solution, or a pH 11.2 aqueous solution was used. The number of the charge transfer cycles for the measurement was 10, 20, 60, or 100 cycles.

As shown in FIG. 10, the pH of the aqueous solution, which was the object measured, was found to be proportional to the output voltage $V_{out}$. It was also found that as the number of the charge transfer cycles was increased, a slope of a regression line increased, leading to an increase in detection sensitivity.

pH Monitoring Experiment

By repeating the measurement cycle (the number of the charge transfer cycles: 100) shown in FIG. 9 using the prepared pH sensor, pH of the solution was monitored.

More specifically, the object 32 to be measured on the sensing section 10 of the extension gate electrode 8 was changed from a pH 6.9 aqueous solution to a pH 2.8 aqueous solution to a pH 6.9 aqueous solution to a pH 11.2 aqueous solution to monitor pH of the aqueous solutions.

Figure 11:
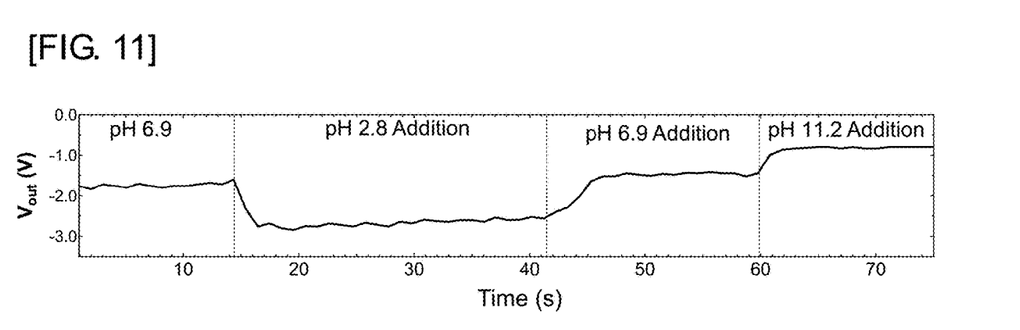
FIG. 11 shows a graph of results of pH monitoring experiments.

The change in the output voltage $V_{out}$ at the time of changing the pH of the object 32 measured is shown in FIG. 11.

From the measurement results shown in FIG. 11, it was confirmed that the output voltage $V_{out}$ changed according to the pH of the object 32 measured.

It was thus confirmed that the pH of the object 32 measured was monitored using the pH sensor prepared.

REFERENCE SIGNS LIST

1, 1*a*, 1*b*: substrate
2: semiconductor thin film
3: injection electrode
4: first gate electrode
5: second gate electrode
6: transfer electrode
7: capacitor
8: extension gate electrode
9: gate portion
10: sensing section
11: wiring portion
13: first contact region
14: first control region
15: sensing region
16: second control region
17: second contact region
18: third control region
20*a* to 20*f*: MIS structure
22: third gate electrode
24: fourth gate electrode
26, 26*a* to 26*d*: insulator layer
28: reset gate electrode
29: reset electrode
30: reference electrode
32: object to be measured
35: charge transfer section
37: source follower circuit
38: wiring
50: chemical sensor

What is claimed is:

1. A chemical sensor comprising: a substrate; a semiconductor thin film provided on the substrate and having a first contact region and a second contact region; an injection electrode in contact with the first contact region; a first MIS structure including a part of the semiconductor thin film and a first gate electrode; a second MIS structure including a part of the semiconductor thin film and a second gate electrode; a transfer electrode in contact with the second contact region; and a capacitor electrically connected to the transfer electrode, wherein
   the semiconductor thin film has a sensing region provided so that an electric potential thereof changes in direct or indirect response to an object to be measured;
   the injection electrode is configured to inject an electrical charge into the first contact region;
   the first MIS structure is configured to control a flow of the electrical charge to the sensing region, the electrical charge being injected into the first contact region by the injection electrode;
   the second MIS structure is configured to control the flow of the electrical charge from the sensing region to the second contact region; and
   the transfer electrode is configured to allow the electrical charge in the sensing region to flow to the capacitor through the second contact region.

2. The chemical sensor according to claim 1, wherein the substrate is a flexible substrate.

3. The chemical sensor according to claim 1, wherein the semiconductor thin film has a thickness that is the same as or thicker than a thickness of a monoatomic layer but is 200 nm or less.

4. The chemical sensor according to claim 1, further comprising an extension gate electrode and a third MIS structure, wherein
   the extension gate electrode comprises a gate portion and a sensing section that electrically interacts directly or indirectly with the object to be measured, and
   the third MIS structure includes the sensing region of the semiconductor thin film and the gate portion.

5. The chemical sensor according to claim 4, further comprising a reference electrode, wherein the reference electrode is placed around the sensing section of the extension gate electrode.

6. The chemical sensor according to claim 1, further comprising a fourth MIS structure, wherein the fourth MIS structure includes the first contact region of the semiconductor thin film and a third gate electrode.

7. The chemical sensor according to claim 1, further comprising a fifth MIS structure, wherein
   the fifth MIS structure includes the second contact region of the semiconductor thin film and a fourth gate electrode, and
   the transfer electrode is in contact with the second contact region of the semiconductor thin film.

* * * * *